United States Patent [19]

Levy

[11] Patent Number: 4,983,389

[45] Date of Patent: Jan. 8, 1991

[54] HERBICIDAL DELIVERY COMPOSITIONS AND METHODS FOR CONTROLLING PLANT POPULATIONS IN AQUATIC AND WETLAND ENVIRONMENTS

[75] Inventor: Richard Levy, Fort Myers, Fla.

[73] Assignee: Lee County Mosquito Control District, Fort Myers, Fla.

[21] Appl. No.: 210,799

[22] Filed: Jun. 24, 1988

Related U.S. Application Data

[63] Continuation-in-part of Ser. No. 32,532, Apr. 1, 1987, Pat. No. 4,818,534.

[51] Int. Cl.$^5$ .......................... A01N 25/34; A61K 9/14
[52] U.S. Cl. ..................................... 424/404; 424/405; 424/408; 424/409; 424/410; 424/78; 424/84
[58] Field of Search ................. 424/405, 408, 78, 409, 424/84, 484, 41 D, 489, 404; 71/3

[56] References Cited

U.S. PATENT DOCUMENTS

| | | | |
|---|---|---|---|
| 3,085,850 | 4/1963 | Egan et al. | 21/60.5 |
| 3,415,614 | 10/1968 | Egan et al. | 21/60.5 |
| 3,535,423 | 10/1970 | Ordas | 424/176 |
| 3,576,760 | 4/1971 | Gould et al. | 424/487 X |
| 3,957,480 | 5/1976 | Kornis | 424/405 X |
| 4,053,627 | 10/1977 | Scher | 424/278 |
| 4,058,124 | 11/1977 | Yen et al. | 424/79 |
| 4,062,855 | 12/1977 | Allan et al. | 424/78 |
| 4,070,348 | 1/1978 | Kraemer et al. | 424/484 X |
| 4,110,431 | 8/1978 | Dita | 424/78 |
| 4,134,863 | 1/1979 | Fanta et al. | 128/285 |
| 4,154,818 | 5/1979 | Kanada et al. | 424/81 |
| 4,160,033 | 7/1979 | Garrett et al. | 424/285 |
| 4,182,620 | 1/1980 | Denninger et al. | 71/65 |
| 4,244,728 | 1/1981 | DelliColli et al. | 424/405 X |
| 4,267,280 | 5/1981 | McCormick | 525/56 |
| 4,304,591 | 12/1981 | Mueller et al. | 424/484 X |
| 4,344,857 | 8/1982 | Shasha et al. | 252/316 |
| 4,349,553 | 9/1982 | Brown | 424/484 X |
| 4,375,535 | 3/1983 | Kightlinger et al. | 424/285 X |
| 4,400,391 | 8/1983 | Connick, Jr. | 71/88 |
| 4,401,456 | 8/1983 | Connick, Jr. | 424/488 X |
| 4,421,759 | 12/1983 | Boisvenue | 424/405 X |
| 4,436,719 | 3/1984 | Lindaberry | 424/407 |
| 4,497,930 | 2/1985 | Yamasaki et al. | 524/556 |
| 4,500,338 | 2/1985 | Young et al. | 424/484 X |
| 4,639,366 | 1/1987 | Heller | 424/484 |
| 4,640,044 | 2/1987 | Varnon | 424/405 X |
| 4,663,341 | 5/1987 | Jacobson | 514/256 X |
| 4,663,346 | 5/1987 | Coulston et al. | 514/456 |
| 4,667,436 | 5/1987 | Benson | 424/405 X |
| 4,677,003 | 6/1987 | Redlich et al. | 71/3 X |
| 4,681,806 | 7/1987 | Matkan et al. | 71/3 X |
| 4,707,359 | 11/1987 | McMullen | 71/3 X |
| 4,722,838 | 2/1988 | Tocker | 424/405 X |
| 4,743,448 | 5/1988 | Bahadir et al. | 424/405 |
| 4,818,534 | 4/1989 | Levy | 424/405 X |
| 4,818,536 | 4/1989 | Meyers et al. | 424/409 |

FOREIGN PATENT DOCUMENTS 2108517  5/1983  United Kingdom .
2141023  12/1984  United Kingdom .

*Primary Examiner*—Thurman K. Page
*Attorney, Agent, or Firm*—Finnegan, Henderson, Farabow, Garrett & Dunner

[57] ABSTRACT

Superabsorbent solid organic polymers which absorb over 100 times their weight in water are used in aquatic and wetland environment plant (weed) population control compositions. Methods for using the solid or flowable, superabsorbent polymer herbicidal delivery agents for the control of aquatic and wetland plant populations, or for the simultaneous or concurrent control of both aquatic plant and aquatic insect (particularly mosquitoes) populations, in an area needing aquatic and wetland environment plant (weed) control treatment, are described.

25 Claims, No Drawings

HERBICIDAL DELIVERY COMPOSITIONS AND METHODS FOR CONTROLLING PLANT POPULATIONS IN AQUATIC AND WETLAND ENVIRONMENTS

CROSS-REFERENCE TO RELATED APPLICATION

This is a continuation-in-part of my application entitled "Improved Insecticidal Delivery Compositions and Methods for Controlling a Population of Insects in an Aquatic Environment," Ser. No. 032,532 filed Apr. 1, 1987 now U.S. Pat. No. 4,818,534.

BACKGROUND OF THE INVENTION

1. Field of the Invention

The present invention relates to a superabsorbent polymer herbidical delivery agent having excellent formulation flexibility, controlled release potential, runoff resistance and hydrodynamic properties.

2. Description of the Prior Art

Infestations of aquatic and wetland plants (weeds) such as hydrilla, southern water-grass, waterhyacinth, watermilfoil, Salvinia etc., have caused detrimental effects on health, agriculture, commerce, and recreation in many areas of the United States and overseas. When present in high densities, these weeds can literally choke lakes and rivers, thereby preventing access by boats and barges. In addition, these weeds can disrupt the functioning of drainage, irrigation, flood control and water conservation projects and hydroelectric power plants, provide breeding grounds for disease carrying mosquitoes and snails, eliminate fishing in certain areas, and alter aquatic ecosystems by preventing sunlight from reaching other plants and animals which live beneath these vegetative mats. Therefore, the growth of these nuisance plant populations must be controlled.

Aquatic and wetland weeds can be controlled by heavy machines (mechanical control) by a variety of insects, pathogens, and other organisms (biological control) by drawdowns, plastic sheets, and colored dyes (cultural control), and, most commonly, by the use of chemical herbicides (chemical control). The concurrent or sequential use of two or more of these control procedures is referred to as integrated control. Solid and liquid herbicide formulations designed for quick and slow or controlled release of the active ingredients are currently in use to control aquatic and wetland plants; however, new formulations are needed that can enhance the efficacy and/or extend the range of performance of existing products.

U.S. Pat. Nos. 4,400,391 and 4,401,456 disclose the use of alginate gel beads to encapsulate bioactive materials to provide for their controlled release. The patent describe beads being made to either float or sink (if used in an aqueous environment) and they may contain herbicides. These beads are also described as acting as carriers to place the bioactive material near the target species, for example, a floating bead containing a herbicide releasing the herbicide in close proximity to floating aquatic weeds, or the beads falling through foliage to release herbicide into the soil. U.S. Pat. No. 4,344,857 involves encapsulation of xanthate derivatives. The encapsulation techniques are complicated, costly and quality sensitive.

A relatively new approach to herbicidal delivery has been by application of controlled release formulation such as described by Richard W. Baker in *Controlled Release of Biologically Active Agents,* 1987, Wiley-Interscience Publishing, 279 pp. This book describes the use of various controlled release technologies including simple diffusion from monolithic devices such as hydrogels. More complex release mechanism include the use of biodegradable matrix carriers, bonding of active ingredients in heterogeneously or homogeneously degradable polymers, called polyagents. Polyagents may actually be polymers formed of monomers of the active agent. The release mechanics of these controlled release mechanisms are complex depending on the presence (and strength) or absence, of degradable ligand bonds and their location of the degradable bonds (e.g., as active agent bonds to the polymer), the concentration of the active agent and/or dispersant or solvent in the carrier, the relative hydrophobicity or hydrophilicity of the polymer, whether or not the polymer degrades homogeneously or heterogeneously, whether the active agent is in the solid form or the liquid form in the polymer, etc.

A relatively new class of polymers has recently been introduced that exhibits remarkable absorbency. However, there has been no recognition of their uses for herbicidal delivery. One example is the acrylic-based superabsorbent polymers The aqueous absorbency mechanism of acrylic-based superabsorbent polymers has been described by the Chemdal Corporation (Arlington Heights, Ill. 60004) in their Technical Data Sheets on Aridall ® Superabsorbent Polymers. The absorbency of acrylic-based superabsorbent polymers is attributed to the carboxylic groups located on the backbone of the superabsorbent polymer. When water contacts their superabsorbent polymer, these groups solvate rapidly and develop mutually repulsive negative charges. This causes the superabsorbent polymer to uncoil and absorb many times its weight in water. Crosslinking prevents solution of the superabsorbent polymer. The aqueous medium rapidly becomes oriented on the surface of the superabsorbent polymer by virtue of hydrogen bonding. The resulting gel has remarkable ability to hold the aqueous medium even under pressure. Superabsorbent polymers hold fluids by a physico-chemical mechanism. Electrolytes/salts interfere somewhat with the hydrogen bonding. Crosslinked acrylic-based superabsorbent polymers always absorb less aqueous medium when electrolytes/salts are present.

Specific Objects

It is therefore an object of the present invention to provide compositions that are solid or flowable, and methods for the dry, moist, semi-aquatic, or aquatic ground or aerial treatment of a variety of aquatic plant (weed) habitats with the composition, which overcomes the problems and deficiencies of the prior art.

It is also an object of the present invention to provide a composition and method, which is easy to prepare (formulate) and use (apply), and which is biodegradable and safe to the environment, but which is effective for use in controlling one or more immature and mature stages of obnoxious or undesirable aquatic and wetland weeds or related vegetation.

It is a further object of the present invention to provide an agglomerated or non-agglomerated solid or variable-viscosity, flowable (aqueous or oil base) composition and method which can incorporate a wide variety of herbicidal, or herbicidal/pesticidal ingredients into a single, stable and homogeneous herbicidal delivery system to control a broad spectrum of aquatic and wetland plant populations and other related habitat pests, and to provide for the variable time release of the active ingredients.

Still another object of the present invention is to provide a method for simultaneously or concurrently controlling two or more natural populations of aquatic and wetland vegetation, and habitat-related pests such as mosquitos and snails with a single, variable-density and/or variable-viscosity herbicidal/pesticidal superabsorbent polymer carrier or matrix delivery formulation.

Still another specific object of the present invention is the provision of incorporating one or more surfactant(s), oil(s), surface-active agent(s) or film-forming agent(s) into a stable and homogeneous, variable-viscosity, flowable herbicidal superabsorbent polymer(s) formulation, the addition of which can slow the rate of release of one or more active ingredients in the herbicidal delivery composition.

Still another object of the present invention is to provide a method for simultaneously or concurrently controlling natural populations of aquatic and wetland plants and habitat-related pests that allows for broadcast coverage with a variety of solid or flowable superabsorbent polymer formulations with conventional application methods without significant losses to wind drift, while enhancing canopy penetration or target substrate adherence.

These and other objects are accomplished by the compositions and method of the present invention.

SUMMARY OF THE INVENTION

The present invention relates to a solid or variable-viscosity flowable (i.e., sprayable, pumpable, injectable) herbicidal delivery composition made from one or more solid superabsorbent polymers with or without water, and with one or more liquid and/or solid herbicides, desiccants, algicides, defoliants, hormones, plant growth regulators, plant growth inhibitors, petroleum oils or solvents, sterilants, biological control agents, microbial control agents, pathogens, or parasites, with or without one or more pesticidal agents, such as insecticides, mosquitocides, schistomacides, molluscicides, ovicides, larvicides, monomolecular films, duplex films, monolayers, petroleum oils, pupicides, biological control agents, pathogens, parasites, microbial control agents, insect growth regulators, conventional toxicants, pesticides, chemosterilants, surface-active agents or film-forming agents, with or without one or more nontoxic adjuvants or diluents such as carriers, binders, deflocculating agents, dispersing agents, penetrants, spreading agents, surface-active agents, surfactants, suspending agents, wetting agents, stabilizing agents, compatability agents, sticking agents, waxes, oils, inverting oils, co-solvents, coupling agents, foams, antifoaming agents, synthetic plastics, elastomers, synergists, natural or synthetic polymers; and other additives and mixtures thereof.

The present invention also relates to a facile method of applying the solid or flowable, aqueous-or oil-base, herbicidal delivery composition with one or more active ingredients, with or without one or more pesticidal and/or nonpesticidal ingredients, to control a variety of aquatic and wetland plants or related vegetation in dry, moist, semi-aquatic, or aquatic environment(s) with conventional ground or aerial techniques.

This invention further relates to a facile method of combining, mixing, encapsulating, agglomerating, or formulating two ingredients, optionally with water or oil, or one or more pesticidal agent(s) and/or various nontoxic adjuvants, diluents or carriers, etc., with one or more superabsorbent polymers into solid powders, dusts, granules, pellets, or briquets, and/or into flowable, variable-viscosity formulations such as sols or semi-gels. The use of superabsorbent polymers in this manner makes possible the mixing or application of herbicidal ingredients with or without additional pesticidal ingredients or other additives that would otherwise be difficult or substantially impossible to combine as joint-or-multiple-action solid or flowable (aqueous-or oil-base) formulations.

In particular, the present invention is directed toward a method of formulating one or more superabsorbent polymer(s) with one or more herbicidal agent(s), with or without water or one or more pesticidal agents or other additives, into solid powders, dusts, granules, pellets or briquets, or into flowable, variable-viscosity sol or semigel-like preemergence or postemergence formulations that can produce quick, slow, controlled, prolonged, or extended release of one or more active ingredients to simultaneously or concurrently control a variety of aquatic and wetland plants such as plankton algae, filamentous algae, submersed weeds, emersed weeds, marginal weeds and floating weeds, while simultaneously or concurrently controlling a variety of other pests such as mosquitoes and snails in dry, moist, semi aquatic, or aquatic habitats with a single application of a solid or flowable multi-product formulation.

Specific Aspects

In accordance with one aspect of the present invention, there is provided an agglomerated or non-agglomerated, solid or variable-viscosity, flowable (aqueous-or oil-base) herbicidal preemergence or postemergence delivery composition for controlling populations of aquatic and wetland weeds (plants) or related vegetation, the delivery composition being applied by ground or aerial techniques (i.e., by aircraft, boats, trucks, etc.) to a variety of dry, moist, semi-aquatic or aquatic habitats. The compositions include at least one superabsorbent polymer, and at least one herbicidal agent, alone or in combination with water, adjuvant(s), diluent(s), or carrier agent(s), or other additive(s), the superabsorbent polymer(s) and herbicidal agent(s) being present in a total amount effective to control the population of aquatic and wetland plants or related vegetation. The diluent(s), adjuvants(s), carrier agent(s), or other additive:(s), if present, is at a concentration adapted to improve formulation component mixing, compatability, and/or stability and/or to allow proper impregnation or mixing of the herbicidal agent(s) on, and/or in, the superabsorbent polymer(s). Preemergence or postemergence herbicidal agents are selected from solid and/or liquid desiccants, herbicides, algicides, petroleum or non-petroleum oils, defoliants, hormones, plant growth regulators, plant growth inhibitors, biological control agents, microbial control agents, pathogens, parasites, and mixtures thereof.

In accordance with another aspect of the present invention, there is provided a solid or flowable, preemergence or postemergence, variable time-release herbicidal delivery composition for controlling a population of aquatic and wetland weeds or related plants which includes one or more superabsorbent polymer(s)

and mixture thereof, at least one herbicidal agent and at least one herbicidal adjuvant, carrier or diluent, the superabsorbent polymer, herbicidal agent(s), and adjuvant(s), carrier(s) or diluent(s) being present in a total amount effective to control the population of aquatic and wetland plants or related vegetation, the variable time-release delivery composition being applied as a ground or aerial treatment to the aquatic and wetland habitat. Carrier, adjuvant, or diluent materials are selected from water, surfactants, alcohols, film-forming agents, surface-active agents, petroleum-or vegetable-base oils, etc., and mixtures thereof, the carrier, adjuvant, or diluent being present at a concentration required to slow, control or vary the rate of release or active components in the solid or flowable, superabsorbent polymer composition.

In accordance with yet another aspect of the present invention, there is provided a solid or flowable, variable time-release herbicidal delivery composition for controlling a population of aquatic and wetland environment plants. The composition includes at least one superabsorbent polymer, at least one herbicidal agent, and at least one additional pesticidal agent, with or without water or additional nontoxic adjuvants, diluents, or other additives. Diluent, adjuvants, or other additive ingredients are selected from surfactants, surface-active agents, film-forming agents, petroleum oils, vegetable oils, suspending agents, wetting agents, penetrants, spreading agents, stabilizing agents, compatability agents, sticking agents, carriers, binders, co-solvents, coupling agents, deflocculating agents, dispersing agents, waxes, oils, synthetic plastics, foams, anti-foaming agents, synergists, elastomers, natural or synthetic polymers, and other additives and mixtures thereof. The superabsorbent polymer(s), herbicidal agent(s), and additional pesticidal agent(s) and adjuvant(s) or diluent(s) are present in a total amount effective to simultaneously or concurrently control the population of aquatic and wetland plants and habitat-related pests, the variable time-release delivery composition being applied as a preemergence or postemergence by ground or aerial treatment to the aquatic and wetland habitat.

In accordance with another aspect of the present invention, there is provided a method for controlling a population of aquatic and wetland environment plants (weeds) or related vegetation which includes the steps of:

preparing or formulating an agglomerated or non-agglomerated, solid or flowable, herbicidal delivery composition which includes at least one superabsorbent polymer and at least one herbicidal agent, with or without water or additional nontoxic adjuvants, diluents, carriers or other additives, by a series of soakings, washes, variable-speed blendings or simple mixing, salt-/electrolyte conditioning treatments or reactions, and-/or temperature and/or moisture conditioning treatments or reactions;

applying said herbicidal delivery composition in an amount effective to control a population of aquatic and wetland plants or related vegetation, the delivery composition being applied by ground or aerial treatment to the aquatic and wetland habitat.

In accordance with still another aspect of the present invention, there is provided a method for simultaneously or concurrently controlling a population of aquatic and wetland plants and related vegetation and habitat-related pests, e.g., mosquitoes and snails. The method includes the steps of:

preparing or formulating an agglomerated or non-agglomerated solid or flowable, variable-viscosity, herbicidal/pesticidal delivery composition which includes at least one superabsorbent polymer, at least one herbicidal agent with or without water, and with at least one additional pesticidal agent and/or nontoxic diluent, adjuvant, carrier, or additive agent by a series of soakings, washes, variable speed blending, salt/electrolyte conditioning treatments or reactions, and/or temperature and moisture conditioning treatments or reactions. Additional pesticidal agents are selected from film-forming agents; monolayers; monomolecular surface films; duplex films; surfactants; surface-active agents; petroleum and nonpetroleum oils; mosquitocides; schistomacides; molluscicides; ovicides; larvicides; pupicides; insecticides; conventional toxicants; pesticides; chemosterilants; biological control agents; microbial control agents; pathogens; parasites; insect growth regulators; and mixtures thereof; and applying said herbicidal/pesticidal delivery composition in an amount effective to simultaneously control a population of aquatic and wetland environment plants and habitat-related pests (e.g., mosquitoes and snails), with the delivery composition being applied by ground or aerial treatment to the aquatic and wetland habitat.

The use of superabsorbent polymer(s) of the present invention provides simple and easy techniques for the incorporation or encapsulation of a variety of herbicidal and herbicidal/pesticidal ingredients into agglomerated or non-agglomerated solid carrier matrices, e.g., dense pellets, granules, or briquets, for the slow or controlled release of active agents in a variety of aquatic and wetland habitats.

Agglomerated or non-agglomerated superabsorbent polymer formulations of the present invention containing one or more diluent or adjuvant surfactant(s), oil(s), surface-active agent(s) or film-forming agent(s), can effect a mechanism for reducing the rate of water absorption (hence superabsorbent polymer swelling), and thereby slow down the rate of release of one or more active agent(s) from the solid matrices, and extend the field life or persistence of the active agent(s) for a period of time greater than would be expected with superabsorbent polymer formulations containing no surfactant(s), film-forming agent(s), surface-active agent(s), or oil(s). Similarly, certain of the flowable, variable-viscosity superabsorbent polymer compositions of the present invention, which are formulated with water and/or one or more surfactant(s), oil(s), surface-active agent(s), or film-forming agent(s), can slow or control the release rate of the active formulation ingredients, while enhancing target substrate adherence and minimizing wind drift loss.

The solid or flowable compositions of superabsorbent polymer(s) will also be suitable with various preemergence herbicidal agent(s), with or without additional pesticidal agent(s) or other additive(s) which can be directly incorporated on, and/or into, dry or moist soil by various techniques (e.g., soil injection). The superabsorbent polymer carrier/diluent/ encapsulation matrix facilitates resistance to surface/subsurface run-off or percolation losses of the active agents. Varied applications from broadcast to point-specific, controlled-release applications against a variety of aquatic weeds can be accomplished by adjusting the agglomeration or formulation process, and/or the specific gravity of the carrier/matrix, and thereby produce formulations that can float and/or sink, or provide broadcast or point-specific coverage for controlled, quick or long-term release. For example, when a dense pellet is employed, the resulting sinking formulation can be evenly distributed over an aquatic environment without herbicidal loss or redistribution problems due to run-off or wind fetch. In addition, variable-viscosity, sprayable, pumpable, or injectable formulations of superabsorbent polymer(s) and one or more surfactant(s), oil(s), surface-active agent(s) or film-forming agent(s), formulated with or without water, can effect a similar mechanism for variable time-release (i.e., slow or controlled release) of active ingredients in floating and/or sinking compositions, thereby extending the field life or persistance of the herbicide(s), with or without additional pesticidal additives, for a greater period of time than would be expected with superabsorbent polymer formulations containing no surfactant(s), oil(s), surface-active agent(s) or, film-forming agent(s). This can extend the field persistence of the active agent(s) in the flowable superabsorbent polymer formulation, and thereby assure that the frequency of costly herbicidal retreatments per habitat will be reduced.

The superabsorbent polymers of the present invention are synthetic organic polymers, which are solid and hydrophilic, absorbing over 100 times their weight in water. Generally, these superabsorbent polymers are chosen from acrylamide and acrylate polymers, copolymers and ter-polymers which are optionally cross-linked or starch grafted acrylonitriles, acrylamide and acrylate polymers, co-polymers and ter-polymers. These superabsorbent polymers are typically in a powder, crystal, or flake form, adapted to be blended and/or agglomerated.

The superabsorbent polymers may be, for example, acrylamide alkali metal or alkali metal/aluminum acrylate co-polymers; polymers; propenenitrile homopolymers, hydrolyzed alkali metal or alkali metal/aluminum salts; polymers of propenamide and propenoic acid, alkali metal or alkali metal/aluminum salts; hydrolyzed acrylonitrile co-polymers and starch graft co-polymers and ter-polymers thereof. All of these are designed to be extremely hydrophilic, absorbing over 100 times their weight in water.

The solid or flowable superabsorbent polymer formulations of the present invention may be composed of one or more of a wide choice of solid and/or liquid herbicidal agents, such as herbicides, algicides, desiccants, defoliants, hormones, plant growth regulators, plant growth inhibitors, petroleum oils or solvents, biological control agents, microbial control agents, pathogens, or parasites, with or without additional pesticidal agents ingredients, such as insecticides, mosquitocides, schistomacides, molluscicides, insect growth regulators, conventional toxicants, pesticides, chemosterilants, film-forming agents, monolayers, duplex films, monomolecular surface films, or petroleum oils, and with or without nontoxic agents such as water, surfactants, spreading agents, adjuvants, carriers, binders, deflocculating agents, dispersing agents, synergists, penetrants, suspending agents, surface-active agents, film-forming agents, sticking agents, wetting agents, stabilizing agents, compatability agents, co-solvents, coupling agents, foams, anti-foaming agents, diluents, waxes, oils, synthetic plastics, elastomers, inverting oils, natural or artificial polymers, and other additives and mixtures thereof; depending on the type or nature of the aquatic and wetland habitat to be controlled, the environmental impact, and/or the plant developmental stage and/or associated insect or pest species to be controlled. The solid or flowable formulations of the present invention are biodegradable. They are also storage stable when formulated, basically as stable as the individual components; however, increased stability may occur in solid matrix form over the flowable form. Solid or flowable superabsorbent polymer formulations of the present invention can take a wide variety of shapes, forms, and consistencies which may be required for a particular application. The solid or flowable superabsorbent polymer formulations of the present invention can have a variable time-release, either quick, or gradual as the situation requires The present invention provides a superabsorbent polymer carrier, suspending, compatability, formulating or encapsulation agent for the variable time-release or delivery of joint-or multiple-active formulations of liquid and/or solid herbicidal and pesticidal agents that would otherwise be difficult or impossible to combine or mix as technical, oil-, or water-base products into a homogeneous solid or flowable formulation.

Solid or flowable, herbicidal superabsorbent polymer formulations of the present invention can be used to control preemergence or postemergence aquatic and wetland weeds or related vegetation in areas that are dry, moist, semi-aquatic or aquatic. Solid or flowable herbicidal superabsorbent polymer formulations of the present invention can also be combined with additional pesticides to simultaneously or concurrently control aquatic and wetlands plants and habitat-related pests such as mosquitoes and snails in a variety of dry (pre-treatment/preemergence), moist, semi-aquatic, or aquatic habitats The solid water-activated compositions have the ability to revert back to a dry state form and return to a wet release form and back again, depending on the habitat and/or climatological temperature/moisture conditions. This ability to transform from a water-active, hydrodynamic release form to an encapsulated dry or moist, inactive, semi-active, or static form, and back again, can help protect the active agents from environmental degradation. This is a distinct advantage of the instant invention. This transformation/retransformation ability can also be found in the flowable compositions; however, to a lesser degree.

Compaction or agglomeration of the superabsorbent polymer matrix of the present invention has been shown to effect a slow or controlled release mechanism for certain active ingredients. Generally, compaction or agglomeration will occur subsequent to mixing/blending with the active agents and various adjuvants. However, water soluble active agents and emulsions can be diffused to the matrix prior to or subsequent to agglomeration, and then reagglomerated or compacted if desired.

In addition, varying the ratio of different types of the superabsorbent polymers used in the present invention, that have differential water uptake or swelling characteristics or specific gravities (e.g., Super Sorb, Aqua Keep ®, Water Lock ®, Aridall ®, and Aquastore ® products) in a single compacted or agglomerated matrix may effect a mechanism to further enhance the controlled release of the active herbicidal or herbicidal/pesticidal ingredients. Furthermore, the addition of adjuvants, carriers, or diluents such as film-forming agents, surface-active agents, oils, or surfactants to the herbicidal or herbicidal/pesticidal formulation can further provide a mechanism to control (i.e., slow) the rate of release of the active ingredients. Specific gravity differences (i.e., less than or greater than one) of the superabsorbent polymers and/or additive active or inert ingredients of the present invention can be readily exploited to develop floating and/or sinking formulations for use in a variety of habitats to kill a variety of aquatic and wetland plants (weeds) or related vegetation, and habitat-related pests.

Other objects, aspects and advantages of the present invention will be apparent to one of ordinary skill in the art from the following:

DESCRIPTION OF THE PREFERRED EMBODIMENTS

Surprisingly, it has been found that certain superabsorbent polymers constitute a novel class of chemicals useful as herbicidal delivery compositions for controlling populations of aquatic and wetland plants or related vegetation in an environment area needing aquatic and wetland plant control treatment.

A herbicidal delivery composition is any composition which can carry, or be adapted to carry, herbicidal agent(s) or herbicidal and pesticidal agent(s), to the target habitat, natural or artificial, aquatic, semi-aquatic, moist, or dry. The herbicidal delivery agent matrix for incorporation into solid or flowable compositions is broadly one or more superabsorbent polymer(s). Superabsorbent polymers as a distinct class of polymers, e.g., starch graft co-polymers, are known in the art. See, for example, those described in U.S. Pat. Nos. 4,375,535 and 4,497,930 (incorporated herein by reference) which are disclosed as useful as adhesives, flocculants, sizes, water-retaining materials for agriculture (e.g., soil conditioners) and water-absorbing materials for sanitary materials. However, the spectrum of advantages attendant the use of superabsorbent polymers in solid and flowable, herbicidal delivery compositions have gone unrecognized.

The superabsorbent polymers of the present invention are synthetic organic polymers which are solid and extremely hydrophilic, absorbing over 100 times their weight in water. Generally, these superabsorbent polymers are chosen from acrylamide and acrylate polymers, co-polymers and ter-polymers or starch grafted acrylonitriles, acrylamide or acrylate polymers, co-polymers or ter-polymer segments. These superabsorbent polymers are typically in an extruded, powder, granule, or flake form, adapted to be blended and/or agglomerated.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000 times their own weight in water (measured using distilled water, pH 7.5, 25° C., 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example the methods described in U.S. Pat. Nos. 4,375,535 and 4,497,930, and can be, for example, the product of grafting corn starch (amylopectin) with acrylonitrile (an acrylic monomer or oligomer).

The superabsorbent polymers can also be propenoic or acrylonitrile/acrylamide-base polymers or co-polymers or ter-polymers that also show superabsorbency properties.

It has also been observed that superabsorbent polymers alone, or impregnated, mixed or combined with one or more herbicidal agent(s), with or without water or one or more pesticidal agents or other additives have the ability to swell differentially in water, and as hydrodynamically active carriers release the impregnated/incorporated substance(s) at varying rates dependent on the type of solid or flowable formulation utilized. Superabsorbent polymers also have the ability under certain conditions to reform or contract to a congealed or crystal-like consistency when evaporation has caused the water to be removed from the sol, gels or jelly-like matrix, and then swell or regel when additional water is added. This ability to resume a functional, or semifunctional, active-agent, encapsulated release form after repetitive periods of wetting and drying, is advantageous for dry or moist preemergence/pretreatment and/or prolonged control release applications of solid or flowable, herbicidal or herbicidal/pesticidal formulations. Specifically, it has been found that when the superabsorbent polymer is impregnated or mixed with a surfactant, surface-active agent, film-forming agent or oil, water will be absorbed at a slower rate, so that active agents in the solid matrix or flowable matrix formulations will be differentially released at slower rates than would be expected with formulations containing no surfactants, etc. This also acts as a restraint on the hydrodynamic activity of the formulation when activated, allowing for deactivation and subsequent reactivation depending on environmental factors.

Non-limiting specific examples of superabsorbent polymers with differential swelling properties, and which are particularly useful in solid or flowable herbicidal or herbicidal/pesticidal delivery formulations include:

(1) a co-polymer of acrylamide sodium acrylate (Terra-Sorb GB);

(2) hydrolyzed starch-polyacrylonitrile (Terra-Sorb);

(3) 2-propenenitrile, homo-polymer, hydrolyzed, sodium salt or poly (acrylamide-co-sodium acrylate) or poly (2-propenamide-co-2-propenoic acid, sodium salt), (Water Lock® Superabsorbent Polymer G-100);

(4) starch-g-poly (2-propenamide-co-2 propenoic acid, sodium salt), (Water Lock® Superabsorbent Polymer A-100);

(5) starch-g-poly (2-propenamide-co-2-propenoic acid, Sodium salt), (Water Lock® Superabsorbent Polymer A-200);

(6) starch-g-poly (2-propenamide-co-2-propenoic acid, mixed sodium and aluminum salt), (Water Lock® Super-absorbent polymer A-222);

(7) starch-g-poly (2-propenamide-co-2-propenoic acid, potassium salt), (Water Lock® Superabsorbent Polymer B-204);

(8) poly (2-propenamide-co-2-propenoic acid, sodium salt), (Water Lock® Superabsorbent Polymer G-400);

(9) poly-2-propenoic acid, sodium salt (Water Lock ® Superabsorbent Polymer J-500 or Aqua Keep ® J-500);
(10) sodium polyacrylate superabsorbent polymers (Aqua Keep ® J-400 and J-550);
(11) starch-g-poly (acrylonitrile) or starch-g- poly (acrylamide -co-sodium acrylate), (General Mills SGP ® 5025);
(12) starch acrylonitrile co-polymer (Super Sorb/AG Sorbent);
(13) cross-linked modified polyacrylamides (Aquastore ® and Aquastore ® F);
(14) cellulosic laminates of poly-2-propenoic acid, sodium salt (Water Lock ® Superabsorbent Laminates L-413, L-415, L-425, L-435, or L-513); and
(15) cross-linked acrylics (Aridall ® 1078, 1080, 1091, 1125, 1092, or 1098).

Superabsorbent polymers are generally nontoxic biodegradable, and relatively inexpensive to buy or produce. See for example, U.S. Pat. Nos. 3,661,815 and 4,159,260 which are incorporated here by reference.

Conventional herbicidals and commercial formulations that may find application in the present solid or flowable, herbicidal delivery compositions include Acrolein, Amitrole, Ammonium Sulfamate, Bromacil, Copper/Copper Sulfate, Dalapon, Dicamba, Dichlobenil, Diquat, Diuron, Endothall, Fenac, Fluridone, Glyphosate, Petroleum Solvents, Picloram, Prometon, Silvex, Simazine, Tebuthiuron, Trichloroacetic Acid, 2,4-D, Velpar, Xylene, Aquazine ®, Aquathol K ®, Aquashade ®, Aqualin ®, Banvel ®, Casoron ®, Cutrine ®-Plus, Cytrol ® Amitrole ®-T, Dichlone ®, Dowpon ®, Endothal ®, Fenac ®, Hydrothal ®-191, Hydrothal ®-47, Hydout ®, K.-Tea ®, Komeen ®, Karmex ®, Monuron ®, Revenge ®, Rodeo ®, Roundup ®, Scout ®, Sonar ®, Spike ®, System E ®, System L ®, Banvel ®-720, Aqualine ®, Ammate ®, Hyvar ®, Cardi ®, Tordon ®, 22K, Primatol ®, Pramitol ®, Juron ®, Aqua Kleen ®, Weedone ®, Velpar ®, Diquat ®, and others and mixtures thereof. These herbicides and herbicidal formulations, the aquatic and wetland plants that they control, effective application rates, etc., are discussed by W. T. Thomson, 1986, in *Agricultural Chemicals, Book II Herbicides,* 1986–87 Revision, Thomson Publications Fresno Calif. 301 pp. and by Dr. Edward O. Gangstad, 1986, in *Freshwater Vegetation Management,* Thomas Publications, Fresno, Calif., 380 pp.

Film-forming agents, surface-active agents, surfactants, or oils, useful in solid or flowable formulations of the present invention as carriers, diluents, adjuvants, release rate modifiers, insecticides, pesticides, etc., are generally organic chemicals that are soluble to essentially insoluble in water. They are nonionic, anionic, or cationic, generally nonvolatile, and can be liquid, semisolid, or solid. They may have a low freezing point and a boiling point above the maximum air temperature of the environment into which they are placed.

Examples of liquid, semisolid, or solid film-forming or surface-active agents useful in conjunction with the present invention for herbicidal and/or herbicidal/pesticidal purposes are: the organic chemicals described in U.S. Pat. No. 4,160,033, which is herein incorporated by reference; and organic chemicals that reduce the water surface tension to greater than 31 dynes/cm and/or have an HLB No. greater than 10. HLB stands for "Hydrophile-Lipophile Balance," as define in THE ATLAS HLB SYSTEM, Atlas Chemical industries, Inc. (4th printing), 1963. The HLB number is an indication of the percentage of the hydrophilic portion of the nonionic emulsifier molecule, as defined on pages 3 and 18 of this reference. Film-forming or surface-active agents such as 2-propanol, tridecyl alcohol, 2-ethyl butanol, 2-ethyl hexanol, 1-hexanol, acetone, xylene, decyl alcohol, polyoxyethylene (20) sorbitan trioleate, polyoxyethylene alkyl aryl ether, polyoxyethylene (5) sorbitan monooleate, isostearyl alcohol containing 10 oxyethylene groups, Morwet ® surfactants, isostearyl alcohol containing 20 oxyethylene groups; cetyl alcohol; stearyl alcohol; or surface-active, petroleum-base oils such as mineral oils, diesel oils, etc., and mixtures thereof may be used.

Various other exemplary surfactants include higher fatty acids, higher alcohol sulfate, alkyl aryl sulfonates, polyoxyethylene sorbitan alkyl ether, polyoxyethylene alkyl phenol ether, polyoxyethylene sorbitan alkyl ester, polyoxyethylene alkylamine, polyoxyethylene aklylamide, poly (oxyethylene-oxypropylene) co-polymer and polyoxyethylene-polyoxypropylene alkylene diamine alkyl trimethyl ammonium salt, alkyl dimethyl benzylammonium salt, alkylpryidinium salt, alkyl betaine or alkyl imidazoline sulfonate.

A herbicidal material is any chemical, agent, or mixtures of chemicals and/or agents used for killing or controlling immature or mature stages of aquatic and wetland plants (weeds), or for severely interrupting their normal growth processes. Herbicidal materials may effect preemergence or postemergence vegetation and can include herbicides, desiccants, algicides, defoliants, hormones, plant growth regulators, plant growth inhibitors petroleum oils or solvents, sterilants, biological control agents, microbial control agents, pathogens and/or parasites.

A pesticidal material is any agent, substance, or mixture of agents and/or substances used to control or kill adult or immature stages of insects (particularly mosquitoes), snails, or other pests or organisms (i.e., cercaria, miracidia) that breed in aquatic and wetland habitats containing aquatic and wetland plants (weeds) or related vegetation. Exemplary pesticidal materials can include insecticides, pesticides, molluscicides, schistomacicides, ovicides, larvicides, pupicides, adulticides, biological control agents, microbial control agents, pathogens, parasites, insect growth regulators, conventional toxicants, chemosterilants, film-forming agents, monolayers, monomolecular surface films, surface-active agents, duplex films, petroleum oils or vegetable oils. Pupicides, larvicides, and insect growth regulators for the control of immature mosquitoes are of specific interest.

A pupicide is any material that can kill that specific developmental stage of certain aquatic insects called a pupa. Pupicides are usually chemicals that kill pupae directly by forming petroleum or non-petroleum films on the surface of water that cause the pupae to drown. This stage is nonfeeding and directly precedes the adult stage. Examples of pupicides useful in accordance with the present invention is Arosurf ® MSF or other film-forming agents described in U.S. Pat. No. 4,160,033, and petroleum oils such as FLIT MLO ®, GB-111 or GB-1356. Biological/microbial pupae control agents such as bacteria, fungi, protoza, viruses, rickettsiae or nematodes may also be used at a future time.

A larvicide is any material that can kill that specific developmental stage of certain aquatic insects called a larva. Larvicides can kill larvae after ingestion of a toxic material, kill on or after contact with the integument, or kill by physical (nontoxic) and/or toxic means by causing the larvae to drown. The larval stage is a feeding stage that usually has several molting or growth phases called instars. For example, in mosquitoes there are four larval instars. The larval stage directly precedes the pupal stage. Examples of larvicides useful in accordance with the present invention include biological control agents or microbial control agents such as *Bacillus thuringiensis* var. *israelensis* (e.g., Vectobac ®, Bactimos ®, teknar ®, Skeetal ®, Mosquito Attack ®) or *Bacillus sphaericus* (e.g., BSP-1); conventional toxicants such as Abate ®, Baytex ®, Dursban ®, Prentox ®, Pyrenone ®, resmethrin, malathion, pyrethrins, allethrin, Baygon ®, Furadan ®, methoxychlor, etc; nonpetroleum film-forming oils such as Arosurf ® MSF; and petroleum oils such as FLIT MLO ®, GB-111, and GB-1356. Fungi (such as *Lagenidum giganteum*, mycelia and oospores), protozoa, viruses, rickettsiae and namatodes may also be used.

Insect growth regulators (IGRs) are chemicals such as juvenile hormone or anti-juvenile hormone analogues that kill the target aquatic environment insect in one or more immature stages by adversely affecting the molting or developmental cycle. IGRs are not considered to be direct larvicides or pupicides. For the most part, larvae that are exposed to the chemical continue to develop normally until they reach the pupal stage where they die. Examples of IGRs are Altosid ®, Dimilin ®, and fenoxycarb (Pictyl ®).

Pesticidal agents (i.e., insecticides, pupicides, larvicides, insect growth regulators, pathogens, etc.) useful in the present invention are discussed in W. T. Thomas, 1985, *Agricultural Chemicals, Book 1 Insecticides*, 1985–86 Revision, Thomas Publications, Fresno, Calif., pp. 1–255, and in George O. Poinar, Jr. and Gerald M. Thomas, 1978, *Diagnostic Manual for the Identification of Insect Pathogens*, Plenum Press, New York, pp. 1–218.

Nontoxic adjuvant or diluent materials include water, carriers, binders, deflocculating agents, penetrants, spreading agents, surface-active agents, surfactants, suspending agents, wetting agents, stabilizing agents, compatability agents, waxes, oils, inverting oils, co-solvents, coupling agents, foams, synergists, anti-foaming agents, synthetic plastics, elastomers, natural or synthetic polymers, and other additives and mixtures thereof.

Aquatic and wetland plants (weeds) and related vegetation can include algae (plankton, blue green, green, filamentous), floating plants, emersed plants, submersed plants, shore, irrigation, and ditch bank plants, and marginal plants or sedges, grasses, and rushes These plants are discussed according to family, genus and species, description, habitat, distribution and importance, etc., by David P. Tarver, John A. Rodgers, Michael J. Mahler and Robert L. Lazor, 1978, *In Aquatic and Wetland Plants of Florida*, Bureau of Aquatic Plant Research and Control, Florida Department of Natural Resources, Tallahassee, Fla., 127 pp. and by Dr. Edward O. Gangstad, in *Freshwater Vegetation Management*, 1986, Thomas Publications, Fresno, Calif., 380 pp.

Normally, when flowable formulations are made by the addition of water or water-based herbicides or herbicides/pesticides formulations to various concentrations of superabsorbent polymers or vice versa, sols or gels of various consistencies (viscosities) or stiffnesses can form that may or may not be flowable. However, high-shear mixing or the addition of various salts/electrolytes can break or interfere with the gel structure or hydrogen bonding, thereby producing flowable (e.g., sprayable) superabsorbent polymer herbicide or herbicide/pesticide aqueous formulations that have the desired viscosity. Viscosity modification will mainly be a function of the active and/or inactive formulation components, the water absorption characteristics of the superabsorbent polymer (i.e., the type and amount of superabsorbent polymers), shear time and strength used to mix the formulation and/or the concentration and type of salts/electrolytes used to modify the sol or gel consistency of the formulation. Therefore, the viscosity of the formulations can be altered to achieve optimum flow ability, droplet size and quantity, and thereby improve the general ground or aerial application characteristics of the formulation for maximum control of the target aquatic plant or pest. Furthermore, active insecticidal ingredients encapsulated in the viscous/semi-viscous, flowable, aqueous superabsorbent polymer formulation can be protected from degradation from the effects of ultraviolet radiation, volatilization, temperature, microbial activity, evaporation, run-off, etc., particularly when used in preemergence/pretreatment habitats Furthermore, evaporation of water from the flowable formulation can result in a solid congealed-like pesticide encapsulated matrix, thereby protecting the active components for prolonged periods until release of the active ingredient(s) is triggered when the habitat is flooded with water.

As briefly discussed above, impregnation or mixing of superabsorbent polymers with fatty alcohol film-forming agents, surface-active agents, surfactants, or hydrophobic oils appears to delay or slow down the rate of water absorption of superabsorbent polymers, thereby providing a useful mechanism for affecting slow or controlled release of herbicidal agents or herbicidal/pesticidal agents from non-agglomerated or agglomerated formulations in aquatic and wetland environments. These agents can be simply incorporated into the non-agglomerated or agglomerated polymer matrix by mixing and subsequent temperature or moisture treatment, thereby entrapping the hydrophobic agent into a matrix. The slow or controlled release process could be further modified or delayed by the degree of compaction of the extruded powdered, crystal, or flaked superabsorbent polymer/herbicidal or superabsorbent polymer/herbicidal/pesticidal agent formulation, by varying the size of an orifice in a container into which the herbicidal delivery composition is placed, by varying the concentration of adjuvants or diluents such as film-forming agent(s), surface-active agent(s), surfactant(s), or oil(s), by varying the concentration of different types of superabsorbent polymers, and by adding one or more binders.

When used in contact with water, the water is differentially held within the gel-like or variable-viscosity, sol-like superabsorbent polymer matrix at a stiffness or strength that is dependent on whether a solid or flowable formulation is used (i.e., the amount of water in the formulation), and therefore evaporates slower than an equivalent amount of superabsorbent polymer-free standing water. Furthermore, the addition of film-forming agents, surface-active agents, surfactants, or oils to the superabsorbent polymer(s) also appears to retard the rate of water loss However, eventually the superabsorbent polymer will restore to a congealed or crystal-like state as compared to its initial dry condition, with loss of active agent dependent on whether it is mixed in an oil, and/or on the climatological/habitat moisture/water to which the formulation is exposed. These observations further suggest additional field persistence mechanisms for variable-time release (controlled release) of any active herbicidal or herbicidal/pesticidal ingredients which are added to the solid or flowable superabsorbent polymer formulations.

It should be noted that certain electrolytes or salts (e.g., alkali metal halides such as sodium chloride, potassium chloride, sodium sulfite, etc.) have been shown to either break down the gel or sol superabsorbent polymer matrix when introduced into water by interfering with hydrogen bonding. Various salts/electrolytes can be added separately or can be included as an integral part of the active ingredient in the herbicidal formulation (e.g., Aquathol ® K contains 40.3% active ingredient as a Dipotassium Salt of Endothall). This has an impact on, and can be used to control the viscosity, swelling and/or water absorbency of superabsorbent polymers, and subsequent population control ability of the herbicidal or herbicidal/pesticidal delivery compositions, i.e., the release rate of certain herbicidal or herbicidal/pesticidal agents that are impregnated therewithin. Furthermore, the salt content of the aquatic habitat can also have an effect on the kill rate of the target species by affecting the solid or flowable superabsorbent polymer water absorbency, bonding, matrix swelling, breakdown, decomposition, and/or release of active herbicidal or herbicidal/pesticidal ingredients, which in combination with salts/electrolytes in the formulation may also affect a mechanism to vary these factors.

Viscous/semi-viscous aqueous compositions can also be rendered flowable by the use of vigorous or high-shear mixing/agitation. Any suitable equipment or technique used to incorporate herbicides or pesticides into an aqueous emulsion can be suitably used to render a non-flowable superabsorbent-base composition flowable. Inverting oil techniques are also appropriate for mixing and dispensing a highly viscous aqueous superabsorbent polymer composition composed of water, at least one herbicidal agent, film-forming agent or oil, with or without pesticides and/or other additives. The degree of mixing/agitation of the aqueous superabsorbent polymer-base aqueous composition will also have an effect on the variable release rate characteristics of active agents by effecting (i.e., breaking or disrupting) the bonding of water with the superabsorbent polymer matrix.

The specific gravity of the delivery composition can be adjusted by the use of solid or liquid surfactants, oils, surface-active or film-forming agents, alcohols, clays, talcs, fillers which can include viscosity modifiers and the like.

The water or surfactant, surface-active agent, film-forming agent, or oil-dissolved, - suspended, or-dispersed active and inactive agents can be incorporated into the superabsorbent polymer as an emulsion. Suitable emulsifying agents can be used to form a stable emulsion, however, an unstable emulsion may be preferred for certain applications. The emulsion can also be rendered somewhat ionic for example, by use of certain surfactants, to promote preferable ionic bonding with the superabsorbent polymers Suitable emulsifiers include those disclosed in U.S. Pat. No. 4,606,773 or any conventional emulsifier such as ammonium lineolate, ethylene oxide adducts, acyl polyglycol ethers, oxyethylated fatty alcohols, alkali metal starches as discussed in U.S. Pat. No. 2,347,680, or starch propionates as disclosed in U.S. Pat. No. 4,059,458. However, any suitable known surfactant, surface-active agent, film-forming agent, or oil can be employed.

The amount of active agent in the delivery composition will depend on the target aquatic and wetland plants or related vegetation, the active herbicidal agent involved, the superabsorbent polymer, whether or not water is present, and whether any additional pesticidal agents, adjuvants and/or diluents are added. Generally, the weight ratio of superabsorbent polymer to herbicidal agent and any additional pesticidal and/or diluent or adjuvant ingredients is from about 0.1:100 to about 100:0.001, the herbicidal agent with or without pesticidal agent being incorporated in the solid or flowable delivery composition for application at rates at or below those rates effective to control the target aquatic plant or pest. The ratio of superabsorbent polymer(s) to any additive diluent or adjuvant such as a surfactant, oil, surface-active agent or film-forming agent is from about 0.1:1 to about 100:1. The ratio of superabsorbent polymer to water in a flowable composition is generally 0.001:100 to 1:1.

EXAMPLES I - II

Bioassays (Table 1) to determine the efficacy of several solid and flowable, superabsorbent polymer herbicidal or herbicidal/pesticidal (insecticidal) formations against floating and submersed aquatic weeds were conducted in 5 gallon plastic containers in a standard greenhouse (3 replications/formulation). Representative target floating or submersed aquatic weeds were duckweed (*Lemna minor*), hydrilla (*Hydrilla verticillata*), and water-hyacinth (*Eichhornia crassipes*). These weeds were obtained from infested canals in Lee County, Fla., and placed in water or soil collected from their aquatic habitats. Aquatic weeds were placed in containers containing 4 gallons of water obtained from the collection sites and allowed to acclimate in a greenhouse for 48 hours prior to the addition of the test herbicidal formulations. Hydrilla were anchored in the soil substrate to a depth of ca. five inches. All containers contained five strands of hydrilla having an average wet weight of 1.1 g per strand (12-15 inches per strand) and duckweed having an average weight of 6.8 g/container. In addition, several containers contained 2 hyacinths at an average diameter of 5-8 inches per plant.

Experimental habitats contained water-hyacinth or combinations of hydrilla and duckweed depending on the range of effectiveness of the herbicide(s) in the formulations. Herbicides used in the solid or liquid superabsorbent polymer formulations were 2,4-D, Sonar ®, Diquat ®, and Diquat ®+ Cutrine ®-Plus. Arosurf ® MSF was formulated in all solid and liquid compositions as a diluent/carrier-spreader and/or potential mosquito larvicide and pupicide; however, mixing compatability tests with other non-pesticidal carrier/diluents such as acetone, hexane, ethyl alcohol, isopropyl alcohol, methyl alcohol and xylene, and mixtures thereof, were also conducted. It should be noted that the mixing compatability of all pesticidal and non-pesticidal carrier/diluents were also evaluated against the herbicides Hydrothol ®-191, and mixtures thereof. The superabsorbent polymers Aqua Keep ® J-500, Aquastore ®, Aquastore ®F, and Water Lock ® A-100 were used in the solid or liquid herbicidal test formulations.

Herbicide(s) or herbicide(s)/insecticide(s) formulations were mixed with or impregnation on/in superabsorbent polymers, with or without water, by vigorous hand-mixing or shaking (0.5 min), with a Dynamixer at 1,800 rpm (0.5 min) and 2,400 rpm (2 min), and/or with a small electrically-powered mixer (G.E. model 420 A) at low speed (2 min). The order of component mixing was dependent on the type of superabsorbent polymers and/or the type of herbicidal/,pesticidal ingredients.

Herbicides were formulated in the solid or flowable compositions for addition to the containers (0.0000157 surface acre) at label-recommended per acre rates (mainly the lowest rate) required to control the target aquatic weed populations. Arosurf ® MSF was mixed with each solid or flowable herbicidal composition for addition to the containers at an application rate of ca. 0.24–0.26 gal per surface acre of water.

Several of the herbicidal/pesticidal formulations were also bioassyed against 4th instar larvae of *Culex quinquefasciatus* to determine the potential mosquito-controlling efficacy of the solid or flowable, superabsorbent polymer herbicidal formulations.

Comparative bioassays (Table 2) to determine the mosquito-controlling efficacy of several solid and flowable, superabsorbent polymer herbicidal/pesticidal compositions were conducted in 400 ml glass beakers (0.000001 surface acre) containing 250 ml of water purified by reverse osmosis filtration (R.O.) and 10 4th instar Culex quinquefasciatus larvae (3 replications/formulation). Application rates of Diquat ®, Diquat ® +Cutrine ®-Plus, 2,4-D, and Arosurf ® MSF were as indicated in the above mentioned container bioassay evaluations. The superabsorbent polymers and Aquastore ® and Aqua Keep ® J-500 were used in solid formulations while Aquastore ® F, Water-Lock ® A-100 were used in the flowable formulations. Solid and liquid compositions were formulated and applied by weight (i.e., lbs per surface acre of water). Larvae were fed a few drops of ground rabbit chow- R.O. water suspension prior to the addition of the test formulations. Bioassays were conducted in a room maintained at 80° F. (ambient) and 80% RH. Data was recorded at 24 hr posttreatment intervals until 100% mortality was recorded Solid herbicidal/mosquitocidal superabsorbent polymer formulation procedures were as follows The desired concentrations of or Diquat ® or Diquat ® and Cutrin ®-Plus and Arosurf ® MSF were added to 400 ml plastic beakers and vigorously hand-mixed with a spatula for ca. 0.5 min. A small electrically-powered mixer (G.E. model 420 A) was used to mix the formulations for an additional 2 min at low speed. This formulation was then stored in airtight ziplock plastic bags until testing Flowable viscous or semi-viscous, herbicidal/mosquitocidal superabsorbent polymer formulations used in the bioassays were prepared in the following manner: The desired concentrations of Aquastore ® F or Water Lock ® A-100 were added to 100 ml plastic beakers. The desired concentration of Arosurf ® MFS was then added to the beakers while vigorously hand-mixing with a spatula for 0.5 min. The desired concentrations of 2,4-D were added to separate 100 ml beakers containing R.O. water and mixed vigorously with a spatula for 0.5 min. The water-base herbicide was then added to a glass 100 ml medicine bottle followed by the addition of the superabsorbent polymer/Arosurf ® MSF mixture. All components were then vigorously hand-shaken for 1 min. Another procedure employed the addition of the desired concentration of a superabsorbent polymer to a 100 ml glass medicine bottle containing R.O. water and vigorously hand-shaken for 0.5 min. Arosurf ® MSF was then added to the mixture and vigorously hand-shaken for an additional 0.5 min. A herbicide was then added and the formulation was vigorously shaken for 1 min. The mixing technique employed was dependent on the type of superabsorbent polymer and/or herbicide used in the formulation.

EXAMPLE I

Results of bioassays concerning the comparative efficacy of several solid, superabsorbent polymer-base herbicidal/mosquitocidal formulations against floating and submersed aquatic plants (weeds) are presented in Table 1. The data indicated that the solid, superabsorbent polymer-base formulations produced generally faster kill (control) of both duckweed and hydrilla when compared to rate of kill that was observed with the technical liquid herbicidal formulations Similar comparative tests with several flowable, superabsorbent polymer-base herbicidal/mosquitocidal formulations were also conducted against floating and submersed aquatic weeds (Table 2). Results indicated that superabsorbent polymer-base herbicidal/mosquitocidal formulations performed as good or better than technical herbicides against duckweed, hydrilla, or water-hyacinth. It should be noted that the viscous or semi-viscous, flowable formulation adhered to the leaves of the water-hyacinth and congealed into an elastomeric or crystal-like matrix as the water evaporated over 24–48 hour period. These matrices were observed to absorb water and swell when the leaves containing the superabsorbent polymer-base formulation died and fell into the water, thereby indicating the protective active ingredient encapsulation/slow-release capacity of the flowable, superabsorbent polymer-base herbicidal/mosquitocidal formulations. It should be noted that non-target tests with Arosurf ® MSF against aquatic and wetland plants indicated that no phytotoxicity should result when technical and water-base Arosurf ® MSF is applied to the water surface around the plants and/or directly on the plants at rates that are at or higher than those recommended on the label for the control of immature mosquitoes (Levy et al. 1981. Ground and aerial application of a monomolecular organic surface film to control salt-marsh mosquitoes in natural habitats of Southwestern Florida. *Mosquito News* 41:291-309; Hester, P. 1984. Field phytotoxicity studies with Arosurf ® MSF. Research Report by the Department of Health and Rehabilitative Services, West Florida Arthropod Research Laboratory, Panama City, Fla.)

EXAMPLE II

Results of bioassays concerning the comparative efficacy of several solid, superabsorbent polymer-base herbicidal/mosquitocidal (Arosurf ® MSF) formulations against fourth instar larvae of *Culex quinquefasciatus* are presented in Table 3. The data indicated that solid superabsorbent polymer-base formulations containing Arosurf ® MSF produced 100% mortality of Culex larvae, pupae, and/or emerging adults within 4–5 days posttreatment, while only 20–27% mortality of immature stages was produced by the technical herbicides. Similar results were observed when flowable, superabsorbent polymer-base herbicidal/mosquitocidal (Arosurf ® MSF) formulations were evaluated against fourth instar larvae of *Culex quinquefasciatus* (Table 4). Results of the bioassays indicated that 100% of the larvae, pupae, and/or emerging adults were killed within 5 days post-treatment while the technical herbicide only produced ca. 53% mortality to the immature stages at this time period.

In general, the data presented in Tables 1–4 indicates that the solid and flowable herbicidal/mosquitocidal superabsorbent polymer-base formulations can be used to simultaneously or concurrently control mixed populations of aquatic weeds and mosquitoes with a single formulation.

TABLE I

Efficacy of solid superabsorbent polymer-based herbicidal formulations against floating and submersed aquatic plants (weeds).

| Test no. | Aquatic Plant(s) | Formulation[1] | Polymer application rate (lbs/acre) | Herbicide application rate[2] (lbs/acre) |
|---|---|---|---|---|
| 1a | Duckweed: Hydrilla | Aqua Keep ® J-500 + Diquat ® + Cutrine ® Plus + Arosurf ® MSF | 35.59 | 21.20 + 12.42 (33.62) |
| b | Duckweed: Hydrilla | Aquastore ® + Diquat ® + Arosurf ® MSF | 68.91 | 21.20 |
| c | Duckweed: Hydrilla | Aquastore ® + Diquat ® + Cutrine ® Plus + Arosurf ® MSF | 35.59 | 21.20 + 12.42 (33.62) |
| d | Duckweed: Hydrilla | Aqua Keep ® J-500 + Diquat ® + Arosurf ® MSF | 23.17 | 21.20 |
| e | Duckweed: Hydrilla | Diquat ® + Cutrine ® Plus | — | 21.20 + 12.42 (33.62) |
| f | Duckweed: Hydrilla | Diquat ® | — | 21.20 |
| g | Duckweed: Hydrilla | Control | — | — |

| Test no. | Arosurf ® MSF application rate[3] (lbs/acre) | Total formulation application rate (lbs/acre) | Comparative stages of plant mortality as indicated by color changes at indicated post-treatment time period (days). (G = Green - normal; PG = Pale Green - 1st stage death; Y = Yellow - 2nd stage death; B = Brown - dead). | | | | | |
|---|---|---|---|---|---|---|---|---|
| | | | 3 | 8 | 12 | 16 | 18 | 21 |
| 1a | 1.97 | 71.18 | PG:G | Y:Y | B:Y | B:B | — | — |
| b | 1.97 | 92.08 | PG:G | Y:Y | B:Y | B:B | — | — |
| c | 1.97 | 71.18 | PG:G | Y:Y | Y:Y | Y:B | B:B | — |
| d | 1.97 | 46.34 | PG:G | Y:Y | Y:Y | B:B | — | — |
| e | — | 33.62 | PG:G | Y:Y | Y:Y | B:B | — | — |
| f | — | 21.20 | PG:G | Y:Y | Y:Y | B:Y | B:Y | B:B |
| g | — | — | G:G | G:G | G:G | G:G | G:G | G:G |

[1]All polymer formulations 1 day old when applied to water; all other formulations prepared on test day.
[2]All herbicides applied to water at rates recommended on the labels.
[3]Arosurf MSF applied to water at a label recommended rate.

TABLE 2

Efficacy of flowable superabsorbent polymer-base herbicidal formulations against floating and submersed aquatic plants (weeds).

| Test no. | Aquatic Plant(s) | Formulation[1] | Polymer application rate (lbs/acre) | Herbicide application rate[2] (lbs/acre) | Arosurf ® MSF application rate[6] (lbs/acre) |
|---|---|---|---|---|---|
| 2a | Duckweed: Hydrilla | Water Lock ® A-100 + Sonar ® + Arosurf ® MSF + R.O. Water | 0.22 | 1.22 | 1.97 |
| b | Duckweed: Hydrilla | Aquastore ® F + Sonar ® + Arosurf ® MSF + R.O. Water | 0.22 | 1.22 | 1.97 |
| c | Water-hyacinth | Water Lock ® A = 100 + 2,4-D + Arosurf ® MSF + R.O. Water | 0.88 | 4.72[3] | 1.97 |
| d | Water-hyacinth | Water Lock ® A-100 + 2,4-D + Arosurf ® MSF + R.O. Water | 1.76 | 9.44[4] | 3.94 |
| e | Duckweed: Hydrilla | Sonar ® | — | 1.22 | — |
| f | Water-hyacinth | 2,4-D | — | 4.72[5] | — |
| g | Duckweed: Hydrilla | Control | — | — | — |
| h | Water-hyacinth | Control | — | — | — |

| Test no. | Water application rate (lbs/acre) | Total formulation application rate (lbs/acre) | Comparative stages of plant mortality as indicated by color and/or morphological changes at indicated posttreatment time period (days). (G = Green - normal; PG — Pale Green - 1st stage death; Y = Yellow - 2nd stage death; B = Brown - dead; BP = Brown around polymer application leaf site(s) - leaf burn; L = Leaf brown and/or detached from plant - 1st stage death beginning | | | | | | | |
|---|---|---|---|---|---|---|---|---|---|---|
| | | | 3 | 8 | 12 | 16 | 18 | 21 | 25 | 27 |
| 2a | 40.7 | 44.11 | PG:G | Y:Y | Y:Y | Y:Y | Y:Y | B:Y | B:Y | B:Y |

TABLE 2-continued

Efficacy of flowable superabsorbent polymer-base herbicidal formulations against floating and submersed aquatic plants (weeds).

| | | | | | | | | | |
|---|---|---|---|---|---|---|---|---|---|
| b | 40.7 | 44.11 | PG:G | Y:Y | Y:Y | Y:Y | Y:Y | B:Y | B:Y | B:Y |
| c | 36.5 | 44.07 | BP/L | BP/L | BP/L | Y | Y | Y | Y | B |
| d | 73.01 | 88.15 | BP/L | BP/L | BP/L | Y | Y | Y | Y | B |
| e | — | — | PG:G | Y:Y | Y:Y | Y:Y | Y:Y | B:Y | B:Y | B:Y |
| f | — | — | PB/L | BP/L | BP/L | Y | Y | Y | Y | B:Y |
| g | — | — | G | G | G | G | G | G | G | G |
| h | — | — | G | G | G | G | G | G | G | G |

[1] Formulations (1 day old) used against duckweed and hydrilla applied to water; formulations (1 day old) used against water-hyacinth applied to leaf surface. All other formulations prepared on test day.
[2] All herbicides applied at rates recommended on the labels.
[3] Two leaves treated at 2.36 lbs/acre.
[4] Two leaves treated at 4.72 lbs/acre.
[5] One leaf treated at 4.72 lbs/acre.
[6] Arosurf ® MSF applied to water at a label recommended rate.

TABLE 3

Efficacy of solid superabsorbent polymer-base formulations of herbicides and Arosurf ® MSF against fourth instar larve of *Culex quinquefasciatus*.[1]

| Test no. | Formulation[2] | Polymer application rate (lbs./acre) | Herbicide application rate (lbs./acre) | Arosurf ® MSF application rate (lbs./acre) | Total formulation application rate (lbs./acre) | \multicolumn{5}{c}{Cumulative percentage mortality of larvae, pupae, and/or emerging adults at indicated posttreatment time period (days).} | | | | |
|---|---|---|---|---|---|---|---|---|---|---|
| | | | | | | 1 | 2 | 3 | 4 | 5 |
| 3a | Aqua Keep ® J-500 + Diquat ® + Cutrine ®-Plus + Arosurf ® MSF | 35.59 | 21.20 + 12.42 (33.62) | 1.97 | 71.18 | 3.3 | 36.7 | 90 | 100 | — |
| b | Aquastore ® + Diquat ® + Arosurf ® MSF | 68.91 | 21.20 | 1.97 | 92.08 | 10 | 50 | 96.7 | 100 | — |
| c | Aqua Keep ® J-500 + Diquat ® + Arosurf ® MSF | 23.17 | 21.20 | 1.97 | 46.34 | 16.7 | 43.4 | 86.7 | 100 | — |
| d | Diquat ® Cutrine ® Plus | — | 21.20 + 12.42 (33.62) | — | 33.62 | 6.7 | 13.3 | 20 | 20 | 20[3] |
| e | Diquat ® | — | 21.20 | — | 21.20 | 3.3 | 10 | 26.7 | 26.7 | 26.7[4] |
| f | Arosurf ® MSF | — | — | 1.97 | 1.97 | 33.3 | 46.7 | 90 | 96.7 | 96.7[5] |
| g | Control | — | — | — | — | 6.7 | 6.7 | 6.7 | 6.7 | 6.7[6] |

[1] Larvae 8 days old at the time of testing.
[2] All herbicides and Arosurf ® MSF applied to water at label recommended rates. All polymer formulations 25 days old at time of testing. All other formulations prepared on test day.
[3,4,5,6] 80, 73.3 3.3, and 93.3% adult escapes, respectively.

TABLE 4

Efficacy of flowable superabsorbent polymer-base formulations of herbicides and Arosurf ® MSF against fourth instar larvae of *Culex quinquefasciatus*.[1]

| Test no. | Formulation[1] | Polymer application rate (lbs/acre) | Herbicide application rate (lbs/acre) | Arosurf ® MSF application rate (lbs/acre) | Water application rate (lbs/acre) | Total formulation application rate (lbs/acre) | \multicolumn{5}{c}{Cumulative percentage mortality of larvae, pupae, and/or emerging adults at indicated post-treatment time period (days).} | | | | |
|---|---|---|---|---|---|---|---|---|---|---|---|
| | | | | | | | 1 | 2 | 3 | 4 | 5 |
| 4a | Water Lock ® A-100 + 2,4-D + Arosurf ® MSF + R.O. Water | 0.88 | 4.72 | 1.97 | 36.5 | 44.07 | 6.7 | 20 | 93.3 | 100 | — |
| b | Aquastore ® F + 2,4-D + Arosurf ® MSF + R.O. Water | 0.66 | 4.72 | 1.97 | 36.7 | 44.05 | 16.7 | 36.7 | 83.3 | 96.7 | 100 |
| c | 2,4-D | — | 4.72 | — | — | 4.72 | 3.3 | 26.7 | 50 | 53.3 | 53.3[3] |
| d | Arosurf ® MSF + R.O. Water | — | — | 1.97 | 41.8 | 43.77 | 16.7 | 46.7 | 83.3 | 96.7 | 100 |
| e | Control | — | — | — | — | — | 0 | 0 | 0 | 0 | 0 |

[1] Larvae 8 days old at time of testing.
[2] All herbicides and Arosurf ® MSF applied to water at label recommended rates. All polymer formulations 25 days old at time of testing; all other formulations prepared on test day.
[3] 46.7% adult escapes.

I claim:

1. A controlled release herbicidal or herbicidal/pesticidal delivery composition for controlling a population of aquatic and wetland plants or related vegetation in dry, moist, semi-aquatic, or aquatic environments comprising: (a) at least one superabsorbent solid organic polymer selected from the group consisting of: hydrophilic acrylamide and acrylate polymers, co-polymers and ter-polymers which absorb over 100 times their weight in water, and (b) at least one formulation containing a herbicidal agent, said polymer and agent being present in a total amount effective to control a target population of aquatic and wetland plants or related vegetation and/or habitat-related pests by ground and/or aerial application techniques and wherein said composition is an admixture formed by mixing the superabsorbent polymer and the formulation containing a herbicidal or herbicidal/pesticidal agent.

2. The controlled release herbicidal or herbicidal/pesticidal delivery composition according to claim 1, wherein said composition is flowable and the weight ratio of superabsorbent polymer to formulation containing a herbicidal or herbicidal/pesticidal agent is from about 0.1:100 to about 100:0.001, the herbicidal or herbicidal/pesticidal agent being incorporated in the flowable delivery composition for application at rates at or below those rates effective to control the target plants or plants and habitat-related pests that are used with the herbicidal or herbicidal/pesticidal agent alone.

3. The composition of claim 1, wherein said superabsorbent polymer comprises a starch graft polymer, co-polymer or ter-polymer.

4. The composition of claim 1, wherein said superabsorbent polymer is selected from the group consisting of: an acrylamide sodium acrylate co-polymer; a hydrolyzed starch-polyacrylonitrile; 2-propenenitrile, homo-polymer, hydrolyzed, sodium salt; poly (acrylamide-co-sodium acrylate); poly (2-propenamide-co-2-propenoic acid, sodium salt); starch-g-poly (acrylonitrile); starch-g-poly (acrylamide-co-sodium acrylate); a starch, regulators, petroleum oils or solvents, sterilants, biological control agents, microbial control agents, pathogens, and parasites.

5. The controlled release herbicidal or herbicidal/pesticidal delivery composition of claim 1, wherein said composition further comprises a container for said superabsorbent solid organic polymer and said herbicidal or herbicidal/pesticidal agent, said container having walls made of at least one water-soluble and/or degradable material.

6. The controlled release herbicidal or herbicidal/pesticidal delivery composition of claim 1, further comprising at least one compound selected from the group consisting of herbicides, desiccants, algicides, defoliants, hormones, plant growth inhibitors, plant growth regulators, petroleum oils or solvent, sterilants, biological control agents, microbial control agents, pathogen, and parasites.

7. The composition of claim 6, further comprising at least one adjuvant, diluent or carrier oil, surfactant, alcohol, surface-active agent, or film-forming agent, with or without other additives such as water, binders, deflocculating agents, dispersing agents, penetrants, spreading agents, suspending agents, wetting agents, stabilizing agents, compatibility agents, sticking agents, waxes, inverting oils, co-solvents, coupling agents, foams, anti-foaming agents, synthetic plastics, elastomers, synergists, natural or synthetic polymers and other additives and mixtures thereof.

8. The composition of claim 7 wherein said oil, surfactant, surface-active agent or film-forming agent is a vegetable-or animal-base oil or fat within which the herbicidal or herbicidal/pesticidal agent(s) is soluble, suspendable or dispersable.

9. The controlled release herbicidal or herbicidal/pesticidal delivery composition of claim 1, further comprising: at least one pesticidal agent selected from the group consisting of insecticides, mosquitocides, molluscidies, schistomacides, avicides, larvicides, monomolecular films, duplex films, monolayers, petroleum oils, pupicides, biological control agents, pathogens, parasites, microbial control agents, insect growth regulators, conventional toxicants, chemosterilants, surface active agents, or film-forming agents, and mixtures thereof.

10. A herbicidal or pesticidal/herbicidal delivery composition for controlling a population of aquatic and wetland plants or related vegetation in dry, moist, semi-aquatic, or aquatic environments comprising: at least one superabsorbent solid organic polymer selected from the group consisting of: hydrophilic acrylamide and acrylate polymers, co-polymers and ter-polymers which absorb over 100 times their weight in water, and at least one formulation containing a herbicidal or pesticidal/herbicidal agent dissolved, suspended, or dispersed in an oil, surfactant, film-forming agent, or surface active agent and/or water, said polymer and agent being present in a total amount effective to control a population of aquatic and wetland plants or related vegetation and/or habitat-related pests, by ground and/or aerial application techniques, and wherein said composition is an admixture formed by mixing the superabsorbent polymer and the dissolved, suspended or dispersed formulation containing a herbicidal or herbicidal/pesticidal agent.

11. The composition of claim 10, wherein the ratio of superabsorbent polymer to film-forming agent, surface active agent, surfactant, or oil is from about 0.1:1 to about 100:1.

12. The composition of claim 10, wherein said superabsorbent polymer comprises an acrylamide, acrylate or acrylic starch graft polymer, co-polymer or ter-polymer.

13. The composition of claim 10, wherein said superabsorbent polymer is selected from the group consisting of: an acrylamide sodium acrylate co-polymer; a hydrolyzed starch-polyacrylonitrile; 2-propenentrile, homo-polymer, hydrolyzed, sodium salt; poly (acrylamide-co-sodium acrylate); poly (2-propenamide-co-2-propenoic acid, sodium salt); starch-g-poly (acrylonitrile); starch-g-poly (acrylamide-co-sodium acrylate); a starch, acrylonitrile co-polymer; poly-2-propenoic acid, sodium salt; poly (2-propenamide-co-2-propenoic acid, sodium salt; starch-g-poly (2-propenamide-co-2-propenoic acid, potassium salt); starch-g-poly (2-propenamide-co-2-propenoic acid); starch-g-poly (2-propenamide-co-2-propenoic acid, sodium salt); starch-g-poly (2-propenamide-co-2-propenoic acid, sodium-/aluminum mixed salts); starch grafted sodium polyacrylates; copolymer acrylamide acrylate; acrylic acid polymers, sodium salt; cellulosic laminates of poly-2-propenoic acid, sodium salt; crosslinked polyacrylamide copolymer; crosslinked modified polyacrylamide; crosslinked acrylics; mixtures thereof and metal salts thereof.

14. The composition of claim 10, wherein said composition further comprises a container for said superabsorbent solid organic polymer and said herbicidal or herbicidal/pesticidal agent, said container having walls made of at least one water-soluble and/or degradable material.

15. The composition of claim 10, further comprising: at least one compound selected from the group consisting of herbicides, desiccants, algicides, defoliants, hormones, plant growth inhibitors, plant growth regulators, petroleum oils or solvents, sterilants, biological control agents, microbial control agents, pathogens, and parasites.

16. A method for controlling one or more population of aquatic and wetland environment plants with or in conjunction with other habitat-related pests comprising the steps of:

preparing a herbicidal or herbicidal/pesticidal delivery composition comprising at least one superabsorbent solid organic polymer selected from the group consisting of hydrophilic acrylamide and acrylate polymers, co-polymers and ter-polymers, which absorb over 100 times their weight in water, and at least one formulation containing a herbicidal or herbicidal/pesticidal agent; and forming an admixture of said superabsorbent polymer and said formulation containing a herbicidal or herbicidal/pesticidal agent; and applying said herbicidal or herbicidal/pesticidal delivery composition in an amount effective to control the population of aquatic and wetland plants or habitat related pests to a dry, moist, semi-aquatic, or aquatic environment area needing plant control treatment or simultaneous plant and pest control treatment.

17. The method of claim 16, wherein said superabsorbent polymer is selected from the group consisting of: an acrylamide sodium acrylate co-polymer; a hydrolyzed starch-polyacrylonitrile; 2-propenenitrile, homopolymer, hydrolyzed, sodium salt; poly (acrylamide-co-sodium acrylate); poly (2-propenamide-co-2-propenoic acid, sodium salt); starch-g-poly (acrylonitrile); starch-g-poly (acrylamide-co-sodium acrylate); a starch, acrylonitrile co-polymer; poly-2-propenoic acid, sodium salt; poly(2-propenamide-co-2-propenoic acid, sodium salt); starch-g-poly )2-propenamide-co-2-propenoic acid, potassium salt); starch-g-poly (2-propenamide-co-2-propenoic acid); starch-g-poly (2-propenamide-co-2-propenoic acid, sodium salt); starch-g-poly (2-propenamide-co-2-propenoic acid, sodium/aluminum mixed salts); starch grafted sodium polyacrylates; copolymer acrylamide acrylate; acrylic acid polymers, sodium salt; cellulosic laminates of poly-2-propenoic acid, sodium salt; crosslinked polyacrylamide copolymer; crosslinked modified polyacrylamide; crosslinked acrylics; mixtures thereof and metal salts thereof.

18. The method of claim 16, wherein said herbicidal agent comprises at least one film-forming agent, surface-active agent, surfactant, or oil, with or without additives, and wherein said superabsorbent polymer comprises a starch graft co-polymer or ter-polymer.

19. The composition of claim 10, further comprising: at least one compound selected from the group consisting of herbicides, desiccants, algicides, defoliants, hormones, plant growth inhibitors, plant growth regulators, petroleum oils or solvents, sterilants, biological control agents, microbial control agents, pathogens, parasites, insecticides, mosquitocides, schistomacides, molluscicides, avicides, larvicides, pupicides, monomolecular films, duplex films, monolayers, petroleum oils, biological control agents, pathogens, parasites, microbial control agents, insect growth regulators, conventional toxicants, chemosterilants, surface-active agents, film-forming agents, binders, deflocculating agents dispersing agents, penetrants, spreading agents, suspending agents, wetting agents, compatibility agents, sticking agents, waxes, inverting oils, co-solvents, coupling agents, foams, anti-foaming agents, synthetic plastics, elastomers, synergists, natural or synthetic polymers and mixtures thereof.

20. The method of claim 16 further comprising, prior to applying to said dry, moist, semi-aquatic, or aquatic environment area, agglomerating said solid superabsorbent polymer and said formulation containing a herbicidal or herbicidal/pesticidal agent, to produce granules, pellets, briquets, or other various shaped solid herbicidal or herbicidal/pesticidal delivery compositions.

21. The method of claim 16, wherein the composition is incorporated on or into dry or moist soil.

22. The method of claim 16 wherein the composition includes a hydrophilic oil, surfactant, surface-active agent, or film-forming agent, to control the herbicidal or herbicidal/pesticidal release rate.

23. The method of claim 16 wherein the agglomerated composition is tempered by exposure to moisture to form a solid.

24. The composition of claim 5 wherein said walls of said container are made of a material selected from at least one of the group consisting of polyvinyl alcohol, polyethylene oxide and hydroxypropyl methyl cellulose.

25. The composition of claim 1 wherein said composition contains water at a polymer to water ratio of about 0.0001:100 to 1:1.

* * * * *

UNITED STATES PATENT AND TRADEMARK OFFICE
CERTIFICATE OF CORRECTION

PATENT NO. : 4,983,389
DATED : January 8, 1991
INVENTOR(S) : Richard Levy

It is certified that error appears in the above-identified patent and that said Letters Patent is hereby corrected as shown below:

Column 1, line 59, "herbicide" should be followed by --,-- (a comma).

Column 2, line 24, "herbicidal" should be --herbicide--;

line 34, "their" should be --the--;

line 55, "composition" should be --composition(s)--; and line 66, "aqueous or oil base" should be --aqueous- or oil-base--.

Column 3, line 4, "time release" should be --time-release--.

Column 4, line 9, "semi-gels" should be --semigels--;

line 30, "semi" should be followed by -- - -- (a hyphen); and line 52, "additive:(s)" should be --additive(s)--.

UNITED STATES PATENT AND TRADEMARK OFFICE
CERTIFICATE OF CORRECTION

PATENT NO. : 4,983,389
DATED : January 8, 1991
INVENTOR(S) : Richard Levy

It is certified that error appears in the above-identified patent and that said Letters Patent is hereby corrected as shown below:

Column 5, line 41, "postemergence" should be followed by --formulation--.

Column 8, line 13, "requires" should be followed by --.-- (a period).

Column 10, line 46, "Sorb GB" should be --Sorb$^{TM}$ GB--;

line 47, "Sorb" should be --Sorb$^{TM}$--; and line 62, "Super-absorbent" should be --Superabsorbent--.

Column 11, line 8, "5025" should be --502s--;

line 11, "cross-linked" should be --crosslinked--;

line 16, "cross-linked" should be --crosslinked--;

line 18, "nontoxic" should be followed by --,-- (a comma);

UNITED STATES PATENT AND TRADEMARK OFFICE
CERTIFICATE OF CORRECTION

PATENT NO. : 4,983,389
DATED : January 8, 1991
INVENTOR(S) : Richard Levy It is certified that error appears in the above-identified patent and that said Letters Patent is hereby corrected as shown below:

line 22, "herbicidals" should be --herbicides--;

line 38, "Tordon®, 22K" should be --Tordon® 22K--;

line 39, "Juron" should be --Kuron--;

line 67, "define" should be --defined--; and line 68, "industries" should be --Industries--.

Column 12, line 19, "ak" should be --alk--;

line 60, "is" should be --are--; and line 2, "111" should be --1111--.

Column 13, line 11, "teknar" should be --Teknar--;

line 18, "111" should be --1111--;

line 52, "rushes" should be followed by --.-- (a period); and

UNITED STATES PATENT AND TRADEMARK OFFICE
CERTIFICATE OF CORRECTION

PATENT NO. : 4,983,389
DATED : January 8, 1991
INVENTOR(S) : Richard Levy It is certified that error appears in the above-identified patent and that said Letters Patent is hereby corrected as shown below:

lines 63-64, "herbicides/pesticides" should be --herbicide(s)/pesticide(s)--.

Column 14, line 14, "flow ability" should be --flowability--;

lines 23-24, "habitats" should be followed by --.-- (a period); and line 65, "loss" should be followed by --.-- (a period).

Column 15, line 53, "fillers" should be followed by --,-- (a comma).

Column 16, line 63, after "Hydrothol®-191," insert --Aquathol®K, Cutrine®-Plus, K-tea®, Velpar®, and Rodeo®--.

Column 17, line 7, ",pesticidal" should be --pesticidal--;

UNITED STATES PATENT AND TRADEMARK OFFICE
CERTIFICATE OF CORRECTION

PATENT NO. : 4,983,389

DATED : January 8, 1991

INVENTOR(S) : Richard Levy

It is certified that error appears in the above-identified patent and that said Letters Patent is hereby corrected as shown below:

line 27, "Culex quinquefasciatus" should be italicized;

line 40, "F." should be "F";

lines 41-42, "recorded" should be followed by --.-- (a period);

line 44, "follows" should be followed by --:-- (a colon);

line 45, "or" should be --polymer,--; and line 52, "testing" should be followed by --.-- (a period).

Column 18, line 19, "formulations" should be followed by --.-- (a period);

line 52, ")" should be followed by --.-- (a period); and

UNITED STATES PATENT AND TRADEMARK OFFICE
CERTIFICATE OF CORRECTION

PATENT NO. : 4,983,389

DATED : January 8, 1991

INVENTOR(S) : Richard Levy

It is certified that error appears in the above-identified patent and that said Letters Patent is hereby corrected as shown below:

line 61, "Culex" should be italicized.

Column 20, Table 1, line 1, "based" should be --base--;

lines 9-16, "® Plus" should be --®-Plus--; and line 22, "post-treatment" should be --posttreatment--.

Column 20, Table 2, line 13, "A=100" should be --A-100--; and line 24, "PG -" should be --PG =--.

Column 21, Table 3, line 2, "quinquefasciatur" should be --quinquefasciatus--;

line 8, (all occurrences) "lbs." should be --lbs--; and line 15, "Diquat® Cutrine® Plus" should be --Diquat®+Cutrine®-Plus--.

UNITED STATES PATENT AND TRADEMARK OFFICE
CERTIFICATE OF CORRECTION

PATENT NO. : 4,983,389
DATED : January 8, 1991
INVENTOR(S) : Richard Levy

It is certified that error appears in the above-identified patent and that said Letters Patent is hereby corrected as shown below:

IN THE CLAIMS:

Claim 4, col. 23, lines 24-27, delete "regulators, petroleum oils or solvents, sterilants, biological control agents, microbial control agents, pathogens, and parasites" and insert:

--acrylonitrile co-polymer; poly-2-propenoic acid, sodium salt; poly (2-propenamide-co-2-propenoic acid, sodium salt); starch-g-poly (2-propenamide-co-2-propenoic acid, potassium salt); starch-g-poly (2-propenamide-co-2-propenoic acid); starch-g-poly (2-propenamide-co-2-propenoic acid, sodium salt); starch-g-poly (2-propenamide-co-2-propenoic acid, sodium/aluminum mixed salts); starch grafted sodium polyacrylates; copolymer acrylamide acrylate; acrylic acid polymers, sodium salt; cellulosic laminates of poly-2-propenoic acid, sodium salt; crosslinked polyacrylamide copolymer; crosslinked modified polyacrylamide; crosslinked acrylics; mixtures thereof and metal salts thereof.--

UNITED STATES PATENT AND TRADEMARK OFFICE
CERTIFICATE OF CORRECTION

PATENT NO. : 4,983,389
DATED : January 8, 1991
INVENTOR(S) : Richard Levy

It is certified that error appears in the above-identified patent and that said Letters Patent is hereby corrected as shown below:

Claim 5, col. 23, lines 30-31, "supe-rabsorbent" should be --super-absorbent--.

Claim 6, col. 23, line 41, "pathogen" should be --pathogens--.

Claim 8, col. 23, line 55, "claim 7" should be followed by --,-- (a comma).

Claim 9, col. 23, lines 63-64, "molluscidies" should be --molluscicides--;

Claim 9, col. 23, line 64, "avicides" should be --ovicides--;

line 68, "surface" should be followed by -- - -- (a hyphen).

Claim 10, col. 24, line 3, "pesticidal/herbicidal should be --herbicidal/pesticidal--;

lines 11 and 12 "pesticidal/herbicidal" should be --herbicidal/pesticidal--;

Claim 10, col. 24, lines 19-20, "supera-borbent" should be --super-absorbent--.

UNITED STATES PATENT AND TRADEMARK OFFICE
CERTIFICATE OF CORRECTION

PATENT NO. : 4,983,389
DATED : January 8, 1991
INVENTOR(S) : Richard Levy It is certified that error appears in the above-identified patent and that said Letters Patent is hereby corrected as shown below:

Claim 11, col. 24, line 24, "surface" should be followed by -- - -- (a hyphen).

Claim 12, col. 24, lines 27-28, "supe-rabsorbent" should be --super-absorbent--.

Claim 12, col. 24, line 29, "acrylate or acrylic" should be --acrylate, acrylic or--.

Claim 13, col. 24, lines 31-32, "supe-rabsorbent" should be --super-absorbent--.

line 34, "2-propenentrile" should be --2-propenenitrile--;

line 41, delete "starch-g-poly (2" and insert --starch-g-poly (2--.

Claim 17, col. 25, line 33, "starch-g-poly )2" should be --starch-g-poly (2--.

Claim 19, col. 26, line 10, "avicides" should be --ovicides--;

UNITED STATES PATENT AND TRADEMARK OFFICE
CERTIFICATE OF CORRECTION

PATENT NO. : 4,983,389
DATED : January 8, 1991
INVENTOR(S) : Richard Levy

It is certified that error appears in the above-identified patent and that said Letters Patent is hereby corrected as shown below:

lines 11-13, delete "petroleum oils, biological control agents, pathogens, parasites, microbial control agents,"

line 15, "agents (2nd occurrence) should be followed by --,-- (comma).

Signed and Sealed this

Twenty-fifth Day of August, 1992

Attest:

DOUGLAS B. COMER

*Attesting Officer*     *Acting Commissioner of Patents and Trademarks*